United States Patent [19]

Grimmer et al.

[11] Patent Number: 4,567,262

[45] Date of Patent: Jan. 28, 1986

[54] PURIFICATION OF RIBOFLAVIN

[75] Inventors: Johannes Grimmer, Grehaa, Denmark; Hans C. Horn, Lambsheim, Fed. Rep. of Germany

[73] Assignee: BASF Aktiengesellschaft, Fed. Rep. of Germany

[21] Appl. No.: 561,467

[22] Filed: Dec. 14, 1983

[30] Foreign Application Priority Data

Dec. 22, 1982 [DE] Fed. Rep. of Germany ....... 3247381

[51] Int. Cl.$^4$ ........................................... C07D 475/14
[52] U.S. Cl. ................................................... 544/251
[58] Field of Search ......................................... 544/251

[56] References Cited

U.S. PATENT DOCUMENTS 2,324,800 7/1943 Pasternack et al. ................ 544/251
2,807,611 9/1957 Howe ................................... 544/251

FOREIGN PATENT DOCUMENTS 0010151 4/1968 Japan .

*Primary Examiner*—Donald G. Daus
*Assistant Examiner*—Diana G. Rivers
*Attorney, Agent, or Firm*—Keil & Weinkauf

[57] ABSTRACT

An improved process for the purification of crude riboflavin which has been prepared by condensation of an N-(D)-ribityl-2-arylazo-4,5-dimethylaniline and barbituric acid or another N-(D)-ribityl-4,5-dimethyl-aniline derivative with a barbituric acid derivative, by dissolving the crude riboflavin in sulfuric acid or phosphoric acid which has been diluted with water and oxidizing the impurities by treating the solution with hydrogen peroxide, or by dissolving the riboflavin in dilute nitric acid at elevated temperature and then isolating the pure riboflavin by precipitation with water, wherein the mineral acid solution of the riboflavin and the oxidizing agent or the solution of the riboflavin in 20 to 70% strength by weight nitric acid is heated extremely rapidly to a temperature at which the solution clearly changes color from greenish to yellow-orange, the solution is kept at this temperature for from 1 to 50, seconds and the oxidation reaction is then interrupted by addition of water.

The best results are achieved in this process if from 20 to 65% strength by weight nitric acid is used simultaneously as the acid and oxidative agent and if, after the change in color, the mineral acid solution, in particular the nitric acid solution, is passed, immediately or after prior interruption of the oxidation reaction by addition of cold water, into hot water at from 90° to 100° C. and the suspension thereby formed is kept at this temperature for about a further 10–30 minutes.

5 Claims, No Drawings

PURIFICATION OF RIBOFLAVIN

The present invention relates to an improved process for highly purifying crude riboflavin (vitamin $B_2$) by oxidative treatment of the crude riboflavin in mineral acid solution, preferably in nitric acid solution.

As is generally known (cf., for example, W. H. Sebrell and R. S. Harris, "The Vitamins; Chemistry, Physiology, Pathology, Methods", 2nd edition, volume V, 1972, Academic Press, page 22), riboflavin (I) is usually prepared synthetically by condensation of an N-(D)-ribityl-2-arylazo-4,5-dimethylaniline (II) with barbituric acid (III).

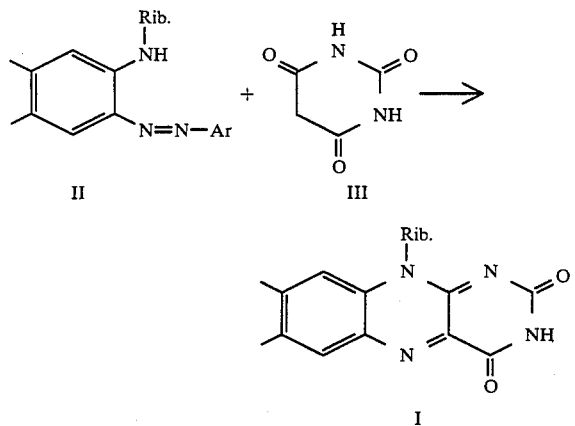

Rib = D-ribityl
Ar = aryl, eg. phenyl

A crude product which, in addition to from about 92 to 96% by weight of I, also contains various impurities, including, for example, barbituric acid, dibarbituric acid, lumiflavin and lumichrome, is obtained in this manner.

Condensation of other N-(D)-ribityl-4,5-dimethylaniline derivatives with barbituric acid derivatives to give riboflavin has also been previously disclosed.

Since isolation of pure riboflavin from the crude material merely by crystallization operations can be effected only with a disproportionately great deal of effort, U.S. Pat. No. 2,324,800 discloses subjecting crude riboflavin to oxidative treatment in an aqueous-acid medium, after which any precipitate is removed and the solution which remains is diluted with a large quantity of water. The riboflavin is here obtained in the form of yellow needles, which need only to be filtered off and washed.

According to the above U.S. Patent, the crude riboflavin is dissolved in a non-oxidative mineral acid, such as hydrochloric acid, sulfuric acid or ortho-phosphoric acid, which has been diluted with not more than two parts by volume of water, the impurities are oxidized by treatment of the mineral acid solution with oxidizing agents, such as chlorine, hydrogen peroxide or chloric acid, insoluble products which have separated out are filtered off and the reaction solution is poured into an excess of water, for the purpose of precipitation of the riboflavin. The above U.S. Patent also proposes using aqueous nitric acid simultaneously as the acid and oxidizing agent. The disadvantages of the known process are the relatively long reaction times and the inadequate degree of purity of the riboflavin precipitate obtained. Thus, for example, the riboflavin is purified with 46% strength by weight nitric acid at from 50° to 60° C. in the course of 3 hours. The impurities which have separated out are then filtered off and the clear solution is poured into hot water at 75° C., an amorphous precipitate being obtained. It is therefore necessary to stir the aqueous suspension at 90° C. for some hours in order to obtain a pure crystalline mass. Apart from the fact that about a further 15% of the riboflavin employed is lost during this procedure, it is time-consuming and technically complicated. The other embodiments in the above U.S. Patent, for example the use of hydrochloric acid and hydrogen peroxide or chlorine, have similar deficiencies.

Japanese Preliminary Published Application 10151/1968 furthermore discloses a process for the preparation of riboflavin by reacting II with III, in which the resulting crude riboflavin is purified by dissolving it in dilute hydrochloric acid, adding hydrogen peroxide solution and then heating the mixture, filtering it and pouring the filtrate into warm water. The disadvantage of this process is that, in spite of the purification, the resulting riboflavin still has an unpleasant odor which causes trouble when the vitamin is used, especially in the human diet.

It is an object of the present invention to eliminate the disadvantages described by improving the oxidative process for the purification of crude riboflavin.

We have found that this object is achieved by an improved process for the purification of crude riboflavin which has been prepared by condensation of an N-(D)-ribityl-2-arylazo-4,5-dimethylaniline and barbituric acid or another N-(D)-ribityl-4,5-dimethylaniline derivative with a barbituric acid derivative, by dissolving the crude riboflavin in sulfuric acid or phosphoric acid which has been diluted with water and oxidizing the impurities by treating the solution with hydrogen peroxide, or by dissolving the riboflavin in dilute nitric acid at elevated temperature and then isolating the pure riboflavin by precipitation with water, wherein the mineral acid solution of the riboflavin and the oxidizing agent, or the solution of the riboflavin in 20 to 70% strength by weight nitric acid, is heated extremely rapidly to a temperature at which the solution clearly changes color from greenish to yellow-orange, the solution is kept at this temperature for from 1 to 100, preferably from 1 to 50 and in particular from 1 to 20, seconds, and the oxidation reaction is then interrupted by addition of water.

Surprisingly, the process according to the invention takes place particularly advantageously if a solution of crude riboflavin in from 20 to 70% strength by weight aqueous nitric acid is heated very rapidly to the temperature at which the solution clearly changes color from greenish to yellow-orange.

We have furthermore found that the best results are achieved in the process according to the invention if the reaction mixture is poured into hot water at from 90° to 100° C. immediately, or after prior interruption of the oxidation reaction by addition of cold water, and the suspension thereby formed is kept at this temperature for about a further 10–30 minutes.

The process according to the invention is based on the surprising observation that oxidative destruction of the impurities takes place in a very limited temperature range within a few seconds, without the sensitive riboflavin itself being noticeably attacked, as is the case in conventional methods.

In an especially advantageous embodiment, the process according to the invention is carried out using aqueous nitric acid simultaneously as the acid and as the oxidative reagent. Apart from the fact that the process is easier to carry out industrially using nitric acid, somewhat better yields and a somewhat purer riboflavin are thereby achieved. Surprisingly, a pure and completely odorless product is obtained here, so that the end product does not have to be washed with methanol, which is unavoidable if, for example, aqueous hydrochloric acid and $Cl_2$ or $H_2O_2$ are used.

In contrast, U.S. Pat. No. 2,324,800 particularly recommends the use of hydrochloric acid and $Cl_2$ or hydrochloric acid and another oxidizing agent which interacts with hydrochloric acid to give $Cl_2$.

The process according to the invention is described in terms of its preferred embodiment, ie. the procedure with aqueous nitric acid. The conditions of the above U.S. patent apply in respect of the nature and concentration of the other mineral acids and of the oxidizing agents.

The oxidation temperature, ie. the temperature at which the color changes, which is also accompanied by vigorous foaming, depends to a certain degree on the nature and concentration of the acid and oxidizing agent. If aqueous nitric acid is used as an acid and oxidative agent, the temperature is a function of the nitric acid concentration. The lower the concentration, the higher the oxidation temperature, and vice versa.

The Table below illustrates this relationship, although deviations may occur in the individual case, depending on the origin of the crude riboflavin.

| Nitric acid concentration % by weight | Temperature of the change in color °C. |
| --- | --- |
| 20 | 98 |
| 30 | 94 |
| 40 | 87 |
| 46 | 84 |
| 50 | 78 |
| 62.5 | 72 |

$HNO_3$ concentrations below 20% by weight are not usually chosen, so that the mixture does not have to be heated to too high a temperature, and concentrations above 70% by weight are generally less advantageous, because destruction of the riboflavin molecule sometimes occurs.

Nitric acid concentrations below 20% by weight and temperatures above 100° C. could be used only if the reaction were carried out in a closed vessel under superatmospheric pressure.

The amount of nitric acid or the concentration of riboflavin in the aqueous nitric acid can vary within wide limits. It is of course most economical to use very little $HNO_3$. If too little $HNO_3$ is used, suspensions are formed instead of solutions. The reaction is advantageously carried out with from 1.5 to 3 parts by weight of the aqueous nitric acid per part by weight of riboflavin.

The amount of aqeuous $HNO_3$ also depends on its concentration. If this is below 10% by weight, the solubility for riboflavin decreases sharply.

Crude riboflavin has the best solubility in nitric acid of concentrations of from 30 to 65% by weight. From about 0.9 to 2 liters of the acid are required here in order to dissolve 1 kg of the crude riboflavin at room temperature. Correspondingly less acid is required if the riboflavin is dissolved at higher temperatures; however, the riboflavin should be completely in solution about 20° C. below the temperature at which the color changes.

Spontaneous oxidative decomposition of the troublesome concomitant substances, without the riboflavin noticeably being attacked, evidently takes place at the temperature at which the color changes. As soon as this temperature has been reached, the reaction should be interrupted without delay, so that the oxidation does not extend to the riboflavin.

The reaction is interrupted by rapid cooling and/or by reducing the oxidation potential of the solution by dilution with water. For this, cold water is added to the reaction solution very rapidly, in an amount of from about 25 to 40% by weight of the solution.

The solution in which the reaction has been braked is advantageously further worked up by introducing this solution into a large excess of boiling hot water. The riboflavin then initially precipitates in an amorphous or apparently amorphous form, but transforms into a crystalline mass in the course of from about 10 to 30 minutes.

From about 4 to 10 liters of boiling water are advantageously used per liter of the nitric acid solution.

When the crystals have formed, which can easily be seen, the mixture is allowed to cool, after which the crystalline mass is separated off and washed with water.

However, the reaction according to the invention can in principle be carried out by interrupting the reaction after the color has changed from greenish to yellow-orange by pouring the solution directly into an excess of water at from 90° to 100° C.

The purification process according to the invention can particularly advantageously be carried out continuously. In the continuous procedure, it is particularly advantageous to pass the mineral acid solution, to which the oxidizing agent has been added, or the nitric acid solution of the crude riboflavin, at a high flow rate through a heated thin tube which, over a length corresponding to a residence time of from about 1 to 50 seconds, is kept at the temperature at which the color changes. The reaction mixture is then immediately passed into boiling water. If the route is too long, the oxidation can also be stopped even in the tube, by metering in cold water.

Observations so far have shown that the temperature at which the color changes is constant for a certain riboflavin quality and constant oxidation solution or at a certain nitric acid concentration, so that it is sufficient to determine this temperature by preliminary experiments. In practice, it is then necessary merely to maintain this temperature or the defined temperature range including this temperature, without further monitoring and control of the reaction being required.

The 100% pure riboflavin is obtained in drug quality in the form of a completely odorless egg yellow powder in a yield of from 94 to 98% of theory, based on the riboflavin content of the crude product, by the process according to the invention.

EXAMPLE 1

40 g of 92.7% pure riboflavin were dissolved in a mixture of 50 ml of 62.5% strength nitric acid and 40 ml of water at 60° C. and the solution was heated rapidly to 90°–92° C. After the reaction solution had foamed and the color had changed from green to yellow-orange, 40 ml of cold water were added immediately. The solution was then poured into 800 ml of boiling hot water. Transformation to crystals took place at this temperature in the course of 20 minutes. After the mixture had been cooled to 30° C., the residue was filtered off with suction and washed with a total of 225 ml of water. After drying, 36.2 g of crystals which fluoresced yellow and contained 100% of riboflavin were obtained, corresponding to a yield of 97.8% of theory, based on the riboflavin content of the crude product.

EXAMPLE 2

11 ml per minute of a solution of 3.49 g of crude riboflavin (92.7% pure) in 9.5 ml of hot 40% strength by weight nitric acid, at 60° C., were pumped through a U-shaped glass tube (internal diameter of 4 mm) heated over a length of 30 cm by means of a heating bath at 120° C. The residence time of the solution in the heated zone, where the oxidation reaction shown by the change in color from green to yellow-orange took place, was 20.6 seconds. Immediately after the heated zone, 4 ml/minute of water were added to the solution via a T-piece, and the solution was then passed to a mixing vessel, which was simultaneously charged with 70 ml/minute of boiling water (95°–98° C.) The suspension which formed here was stirred in this vessel at from 95° to 98° C., with an average residence time of 15 minutes, before being continuously discharged.

After cooling to 30° C., filtration, washing with water and drying, 185.3 g of 100% pure riboflavin/hour were obtained. This corresponds to a yield of 95.4% of theory, based on the riboflavin content of the crude product.

We claim:

1. An improved process for the purification of crude riboflavin which has been prepared by condensation of an N-(D)-ribityl-2-arylazo-4,5-dimethylaniline and barbituric acid or another N-(D)-ribityl-4,5-dimethylaniline derivative with a barbituric acid derivative, by dissolving the crude riboflavin in sulfuric acid or phosphoric acid which has been diluted with water and oxidizing the impurities by treating the solution with hydrogen peroxide, or by dissolving the riboflavin in dilute nitric acid at elevated temperature and then isolating the pure riboflavin by precipitation with water, wherein the mineral acid solution of the riboflavin and the oxidizing agent, or the solution of the riboflavin in 20 to 70% strength by weight nitric acid, is heated extremely rapidly to a temperature at which the solution clearly changes color from greenish to yellow-orange, the solution is kept at this temperature for from 1 to 100 seconds and the oxidation reaction is then interrupted by addition of water.

2. A process for the purification of crude riboflavin as claimed in claim 1, wherein a solution of crude riboflavin in from 20 to 70% strength by weight nitric acid is heated very rapidly to the temperature at which the solution clearly changes color from greenish to yellow-orange.

3. A process for the purification of crude riboflavin as claimed in claim 1, wherein, after the change in color, the nitric acid solution is passed immediately, or after prior interruption of the oxidation reaction by addition of cold water, into hot water at from 90° to 100° C., and the suspension formed is kept at this temperature for about a further 10–30 minutes.

4. A process for the purification of crude riboflavin as claimed in claim 1, wherein the solution is kept at the temperature at which the solution clearly changes color from greenish to yellow-orange for from 1 to 50 seconds.

5. An improved process for the purification of crude riboflavin which has been prepared by condensation of an N-(D)-ribityl-2-arylazo-4,5-dimethyl-aniline and barbituric acid, by dissolving and treating the crude riboflavin with aqueous nitric acid at elevated temperature and then isolating the pure riboflavin by precipitation with water, wherein the nitric acid solution is heated very rapidly to a temperature at which the color of the solution clearly changes from greenish to yellow-orange, and, after the change in color, the nitric acid solution is passed, immediately or after prior interruption of the oxidation reaction by addition of cold water, into hot water at from 90° to 100° C., and the suspension which forms is kept at this temperature for about a further 10–30 minutes.

* * * * *